United States Patent [19]

Connolly

[11] Patent Number: 5,252,491
[45] Date of Patent: Oct. 12, 1993

[54] AQUEOUS CARBON DIOXIDE MONITOR

[75] Inventor: Dennis J. Connolly, Alliance, Ohio

[73] Assignee: The Babcock & Wilcox Company, New Orleans, La.

[21] Appl. No.: 666,272

[22] Filed: Mar. 7, 1991

Related U.S. Application Data

[63] Continuation-in-part of Ser. No. 499,142, Mar. 26, 1990, Pat. No. 5,068,090.

[51] Int. Cl.$^5$ .............................................. G01N 27/06
[52] U.S. Cl. ................................ 436/133; 422/82.02; 422/90; 436/68; 436/150
[58] Field of Search ................. 422/82.02, 90; 436/68, 436/133, 150; 324/438, 439, 450

[56] References Cited

U.S. PATENT DOCUMENTS

| | | | |
|---|---|---|---|
| 2,950,176 | 8/1960 | Thayer et al. | 436/150 |
| 4,517,135 | 5/1985 | Szerenyi et al. | 261/104 |
| 4,801,551 | 1/1989 | Byers et al. | 436/68 |

*Primary Examiner*—Lyle Alexander
*Attorney, Agent, or Firm*—Vytas R. Matas; Robert J. Edwards; Daniel S. Kalka

[57] ABSTRACT

An apparatus and method for the measurement of low levels of carbon dioxide in a sample employing membrane separation and ion-exchange technology. The difference in acid strength of carbonic acid and other acids is exploited by treating the sample with a weak base in a membrane separator (10). In this manner, the carbonic acid is distinguished from the stronger acids.

4 Claims, 6 Drawing Sheets

AQUEOUS CARBON DIOXIDE MONITOR

This application is a continuation-in-part of application Ser. No. 07/499,142, filed Mar. 26, 1990, now U.S. Pat. No. 5,068,090 granted Nov. 26, 1991.

BACKGROUND OF THE INVENTION

1. Field of the Invention

The present invention relates in general to the measurement of low levels of carbon dioxide dissolved in water, and in particular, is directed to a method and apparatus for measuring low levels of carbon dioxide dissolved in water employing membrane separation and trans-membrane ion exchange techniques.

2. Description of the Related Art

In monitoring power plant water chemistry, there are three electrical conductivity measurements of interest. These are specific conductivity, cation conductivity, and degassed cation conductivity.

The electrical conductivity or conductivity, which is a measure of the ionic content of a sample, is a non-specific measurement in that all of the ions in solution, both cations and anions, contribute to the total observed conductivity. Specific conductivity is the conductivity measurement obtained from an untreated sample. When the sample is passed through a cation exchange column, which exchanges all cations in solution for the most highly conductive cation, i.e., the hydrogen ion, the cation conductivity is then measured. After the sample passes through the cation exchange column, all of the anions are in their acid form. The degassed cation conductivity measurement is normally the third in this series of three conductivity measurements.

The degassed cation conductivity is a measure of the cation conductivity of a sample after all of the volatile substances which contribute to the conductivity are removed. Normally, the solution is heated to near the boiling point of water to expel carbon dioxide and the other volatile components. The conductivity of the sample is measured at the high temperature and one of several algorithms is used to relate the high temperature conductivity to the room temperature conductivity. Alternatively, the degassed sample can be cooled to room temperature before measuring the conductivity.

The current method for measuring low levels of carbon dioxide dissolved in water is the degassed cation conductivity method which is also known as the re-boiler method. This method assumes that the mal,n volatile constituent contributing to conductivity is the dissolved carbon dioxide which exists in solution as carbonic acid. In this way, the degassed cation conductivity when compared to cation conductivity is an indication of the carbon dioxide content of the sample. In power plants, these measurements allow for distinguishing conductivity increases due to cooling water leaks and air leakage.

There are several disadvantages to the degassed cation conductivity method. The first is that the method does not selectively remove carbon dioxide. At the high temperature, other volatile species are also driven off as well as the carbon dioxide. These include anions of interest like chloride and sulfate which have been converted to the more volatile hydrochloric acid and sulfuric acid by the cation exchange. A key premise of the degassed cation conductivity method is that these other anions are unaffected by the heating process.

Another disadvantage is that the method is probably incomplete. An air saturated water sample contains approximately 0.5 to 1 ppm of total carbonate depending on temperature and pressure from the carbon dioxide in the air. In solution, carbon dioxide is distributed among several forms including carbonate ($CO_3^{-2}$), bicarbonate ($HCO^-_3$), carbonic acid ($H_2CO_3$), and carbon dioxide in various forms of hydration. The volatile forms are the non-ionic species. At a pH of 5.7, which is a typical value for air saturated water, the non-volatile carbonate and bicarbonate constitute about 20% of the total carbonate content. Thus, at any one time, only 80% is available for removal due to volatility. Under static conditions, as carbon dioxide is removed, the 20% non-volatile portion is shifted toward the volatile forms and 100% removal is theoretically achievable. However, this method is a flowing system. Slowing the flow to aid in efficiency of carbon dioxide removal also increases the opportunity to boil off other anions leading to an erroneous result.

Still another disadvantage is that useful results require the determination of small differences in conductivity. For example, in a solution which is a 300 ppb chloride (as HCL) and 500 ppb carbonate, the theoretical conductivity is 3.764 microsiemens per centimeter ($\mu S/cm$). If all the carbonate is removed, the conductivity due to 300 ppb chloride is 3.607 $\mu S/cm$. Thus, the carbon dioxide content of the sample is measurable by a difference of only 0.157 $\mu S/cm$.

A further disadvantage of the degassed cation conductivity method is that a practical interpretation of the conductivity measured at the outlet relies on a mathematical relationship between the conductivity at 98° C. and the corresponding room temperature conductivity. The alternative method of cooling the sample back to room temperature before measurement introduces the possibility of readmitting carbon dioxide to the sample through air ingress. Additionally, the high temperature process may result in corrosion, the conductive products of which will give erroneously high conductivity measurements.

Thus, there is a need for an apparatus and method which measures low levels of carbon dioxide dissolved in water without the disadvantages of the degassed cation conductivity method. A method is needed where conductivity measurements are taken at an ambient temperature to eliminate reliance on mathematical algorithms for conversion of data and which eliminates concern from potentially interfering high temperature reactions. There is a need for higher precision in the interpretation of measured data to provide confidence and useful results in measuring carbon dioxide content of the sample by increasing the conductivity measurements.

While it is known in ion chromatography how to suppress high background conductivity with membrane based cation exchange systems for greater sensitivity, heretofore there are no methods available with trans-membrane ion exchange techniques that allow for the measurement of low levels of carbon dioxide in water.

SUMMARY OF THE INVENTION

The present invention solves the aforementioned problems with the prior art as well as others by providing a method and apparatus for measuring low levels of carbon dioxide dissolved in water. The present invention utilizes membrane separation and trans-membrane ion exchange techniques to exploit the difference in acid strength between carbonic acid (aqueous carbon dioxide) and other acids typically found in cation exchange effluent.

Accordingly, the present invention provides a method and apparatus for measuring low levels of carbon dioxide dissolved in water.

In the present invention, a sample is passed through a cation exchange column. The effluent is passed through a membrane separator where it is treated with a weak base. The solution exiting the membrane separator consists of the sodium salts of the strong acids but the remaining carbonic acid is unaffected. Prior to entering the membrane separator, the conductivity of the sample is measured. Next, the solution exiting the membrane separator has its conductivity measured. The two conductivity measurements, one before and one after treatment with the weak base, are then used to determine the carbon dioxide concentration of the sample. This determination is made by solving a set of simultaneous equations which describe the chemical systems at each point in the process.

An algorithm contained on a Lotus ® (spreadsheet solves these simultaneous equations. Input to this algorithm are the conductivity measurements before and after the membrane separator.

An aspect of the present invention is to provide an apparatus and method for measuring low levels of carbon dioxide dissolved in water based on a combination of membrane separation and ion exchange processes.

Still another aspect of the present invention is to take conductivity measurements at ambient temperature to eliminate the reliance on mathematical algorithms for the conversion of high temperature data.

The various features of novelty characterized in the present invention are pointed out with particularity in the claims annexed to and forming a part of this disclosure. For a better understanding of the invention, the operating advantages attained by its use, reference is made to the accompanying drawings and descriptive matter in which a preferred embodiment of the present invention is illustrated.

DESCRIPTION OF THE PREFERRED EMBODIMENT

The present invention resides in a method and apparatus for the measurement of low levels of carbon dioxide dissolved in a sample such as water. It is based on a combination of membrane separation and ion exchange processes. The present invention exploits the difference in acid strength between carbonic acid, i.e., aqueous carbon dioxide, and other acids typically found in cation exchange effluent.

Chemically, carbonic acid differs from other acids in a typical cation exchange effluent in that it is only partially ionized. It is referred to as a weak acid as compared to acids like hydrochloric or sulfuric which are totally ionized in water. This is the reason that the contribution of carbonic acid to the total conductivity is relatively minor so that even if carbonic acid could be selectively and completely removed, the resulting change in conductivity is small. The difference in acid strength is exploited in that neutralization reactions selectively discriminate between the strong and the weak acids through the use of different base strengths as neutralizing agents. The following equation represents the reaction between a weak acid and a weak base:

$$H_2CO_3 \;+\; Na_2SO_4 \;\longrightarrow\; \text{Negligible Reaction} \qquad (1)$$
(Weak Acid)   (Weak Base)

The extent to which reaction 1 takes place depends on both the acid and the base strength and the concentrations of the reactants. With the selection of a weak base strength and concentration, the reaction proceeds to only a negligible extent.

The reaction of a strong acid and a weak base is depicted in the following manner:

$$HCl \;+\; Na_2SO_4 \;\longrightarrow\; NaCl + H_2SO_4 \qquad (2)$$
(Strong Acid)   (Weak Base)   (Complete Reaction)

A combination of the first and the second reactions is illustrated with a solution consisting of a strong acid, a weak acid, and a weak base. The strong acid is completely neutralized by being converted to its sodium salt while the weak acid remains unaffected as follows:

$$HCl + H_2CO_3 + Na_2SO_4 \rightarrow NaCl + H_2SO_4 + H_2CO_3 \qquad (3)$$

The present invention exploits the difference in acid strengths illustrated in the above neutralization reactions to selectively discriminate between the strong and weak acids.

For the above reactions to be useful to the present invention, it is desirable to keep the reactants separate but allow only the exchange reaction, that is the hydrogen ions for sodium ions to take place. In this way, the conductivity of the acids as sodium salts may be measured without interference from the bases and their counter ions.

The term "strong base" is defined as a base which completely dissasociates in water. An example of a strong base is sodium hydroxide. A "weak base" only partially dissociates and the degree of dissociation is defined by a dissociation constant, $K_b$, as follows:

$$Base + H_2O \rightleftharpoons Base^+ + OH^- \qquad (4)$$

$$K_b = \frac{[Base^+][OH^-]}{[Base]} \qquad (5)$$

The degree of neutralization between a hypothetical acid, HA, and a hypothetical base, BOH, depends on both the acid and base strengths as follows:

$$HA + BOH \rightleftharpoons H_2O + AB \tag{6}$$

The equilibrium constant, K, for this neutralization reaction is a function of the acid dissociation constant, $K_a$, the base dissociation constant, $K_b$, and the water dissociation constant, $K_w$, as follows:

$$K = \frac{K_a K_b}{K_w} \tag{7}$$

Thus, the degree of neutralization may be controlled by choosing acids and bases of particular strength depending on the extent of neutralization which is desired.

Figure 4:
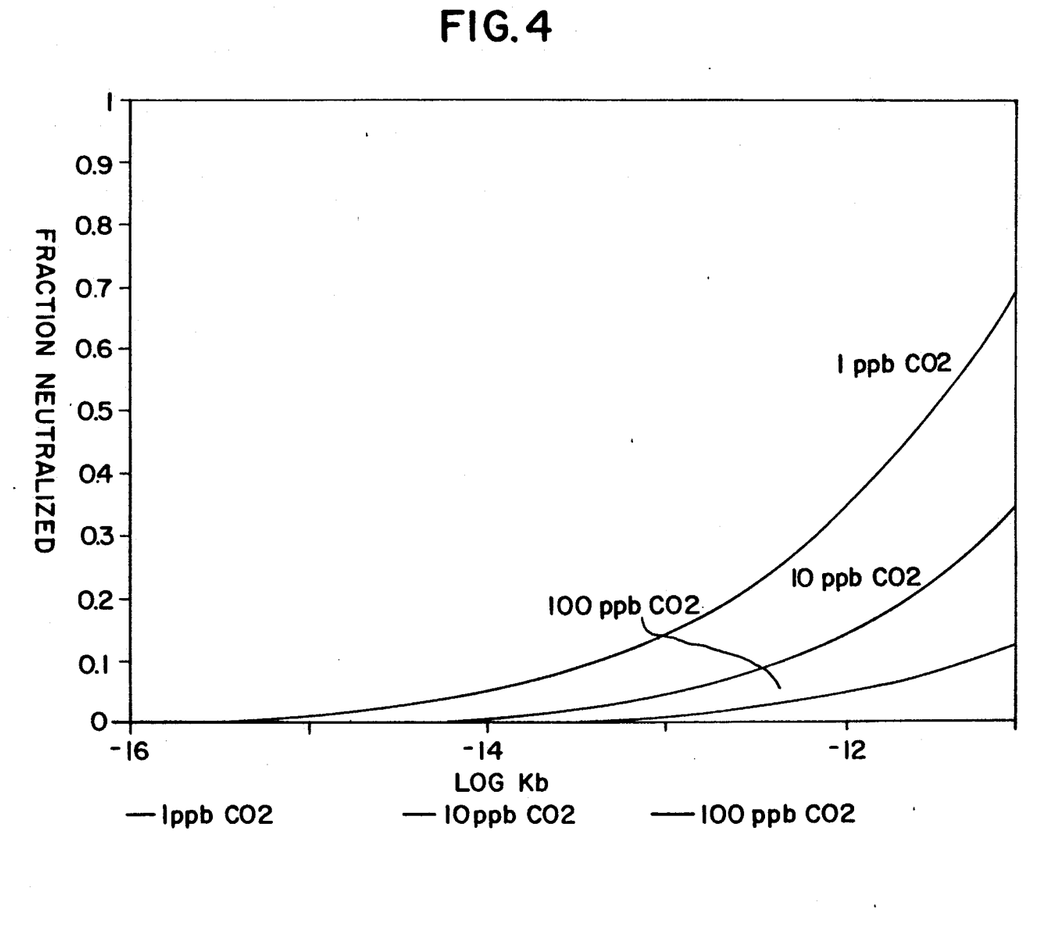
FIG. 4 is a graph showing how base strength may be selected to achieve a desired low degree of neutralization.
Figure 5:
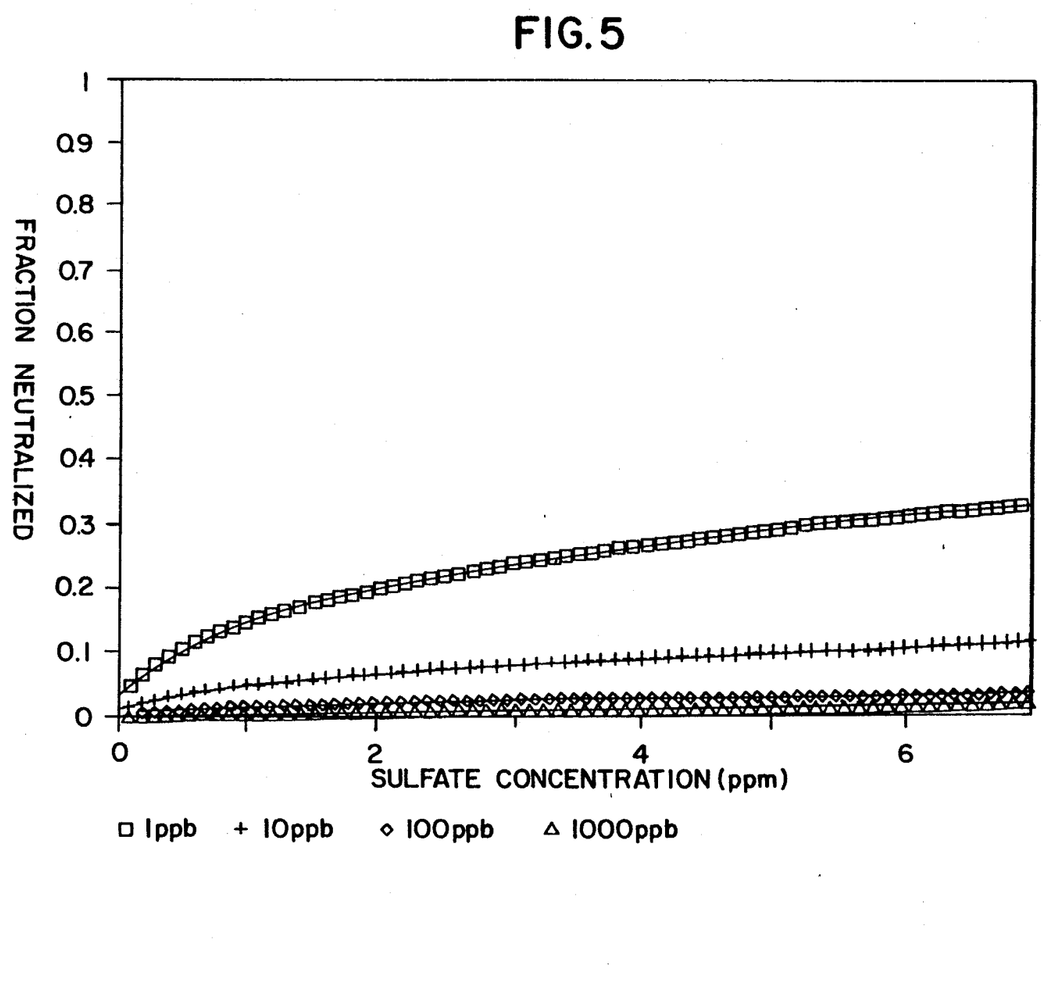
FIG. 5 is a graph showing how the degree of neutralization of carbonic acid using sodium sulfate may be kept to a specified low value.

For carbonic acid in a cation exchange effluent to remain substantially unreacted (un-neutralized), a base is chosen whose strength (dissociation constant) will keep the neutralization equilibrium value to a low or negligible value. FIG. 4 shows how a particular base strength may be selected to achieve a desired low degree of neutralization. FIG. 5 shows how the degree of neutralization of carbonic acid using sodium sulfate may be kept to a specified low value.

Figure 1:
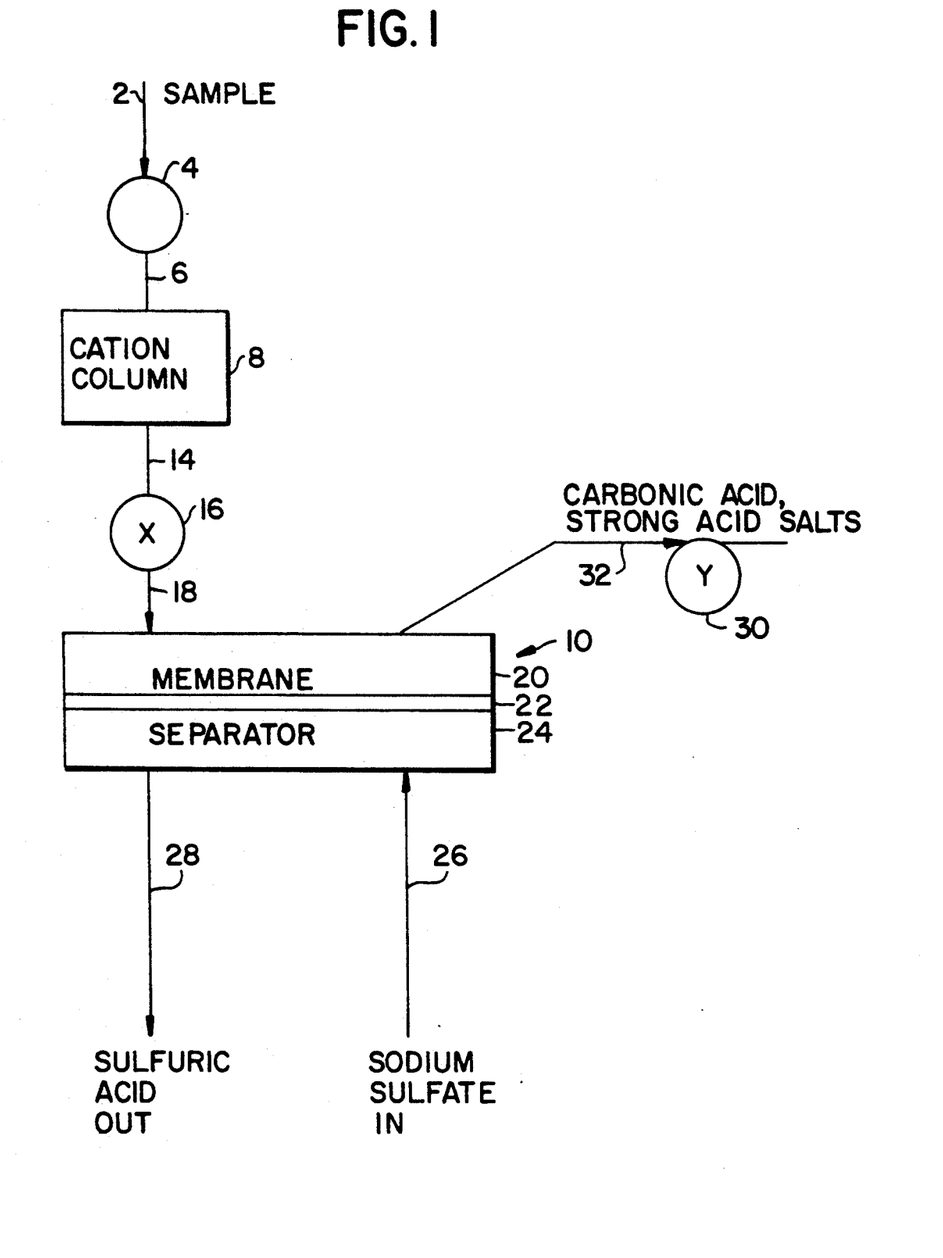
FIG. 1 is a schematic illustration of the present invention.

In the preferred embodiment depicted in FIG. 1, there is a membrane separator (10). The membrane separator (10), has two compartments (20, 24) separated by a membrane (22) which allows for the exchange of ions. The sample stream (2) flows into conductivity cell (4) which measures the conductivity of the untreated sample to give specific conductivity. The specific conductivity of the untreated sample stream is optional. A cation exchange column (8) receives the sample stream (2) from line (6). After the sample stream (2) passes through column (8), it flows through a conductivity cell (16) which measures the sample conductivity. This is the traditional cation conductivity. The sample proceeds along line (18) to the first compartment (20) of the membrane separator (10). Within the membrane separator (10), a weak base such as sodium sulfate flows counter to the flow of the sample on the opposite side of the membrane (22) in the second compartment (24) of the membrane separator (10). The weak base enters the membrane separator (10) by way of line (26) and exits via line (28). In the membrane separator (10), membrane (22) allows sodium ions to be exchanged for hydrogen ions. The reaction as set forth in Reaction 3 occurs and the acid formed from the reaction exits via line (28) while the solution exiting the compartment (20) consists of the sodium salts of the strong acids with the carbonic acid in the sample being unaffected.

As the solution exits the membrane separator (10) via line (32), conductivity cell (30) measures the conductivity of the solution.

EXAMPLE 1

Figure 3:
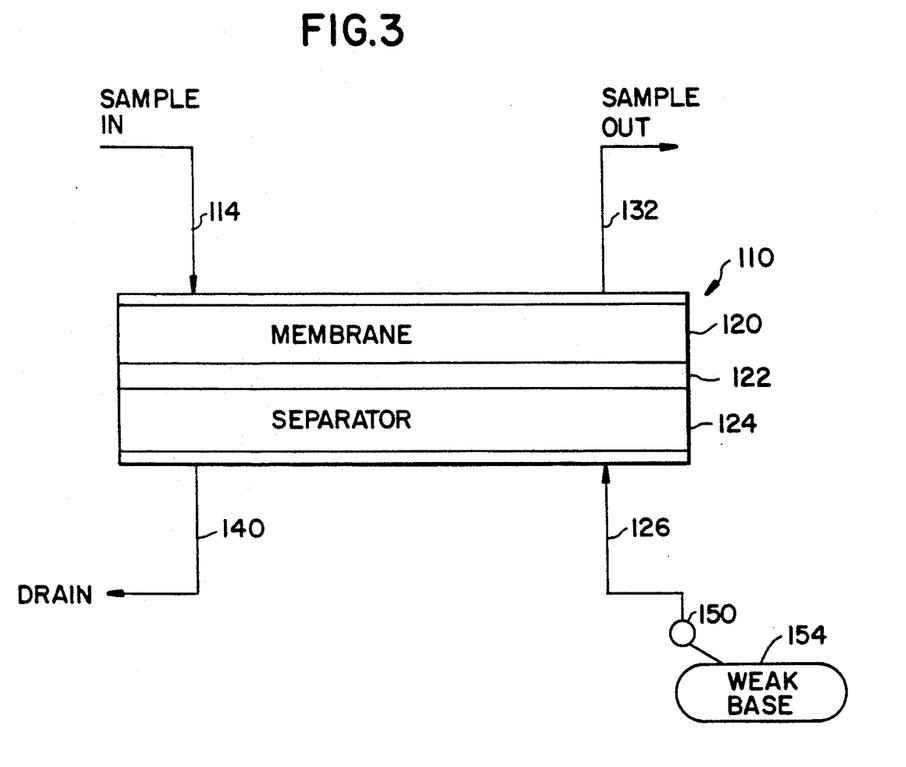
FIG. 3 is a schematic illustration of an alternate embodiment of the present invention.

The concept of the present invention was demonstrated on the embodiment depicted in FIG. 3. In FIG. 3, the sample solution is pumped through a single membrane separator (110). The membrane separator (110) consists of a first compartment 120) separated by a membrane (122) from a second compartment (124). Weak base (154) flows, either by a pump or from a pressurized reservoir, through compartment (124) of the membrane separator. The conductivity before and after the membrane separator (110) is measured with a conductivity cell (not shown). This embodiment is operated in accordance with the description of the preferred embodiment shown in FIG. 1.

A sample pump causes the sample stream to flow through membrane separator (110). A Bowdine Electric Company fractional horse power gearmotor was used. The conductivity cells were manufactured by Beckman Instruments. The conductivities were measured with a Leads and Northrup electrolytic conductivity bridge. The membrane separator (110) employed was a Dionex Anion Micro Membrane Suppressor (AMMS). The reagent base (154) was stored in a five liter plastic carboy which was pressurized with nitrogen to provide flow through the membrane separator (110).

The sample solution consisted of varying amounts of carbonic acid which was produced by passing solutions of sodium carbonate through a cation exchange column.

Figure 6:
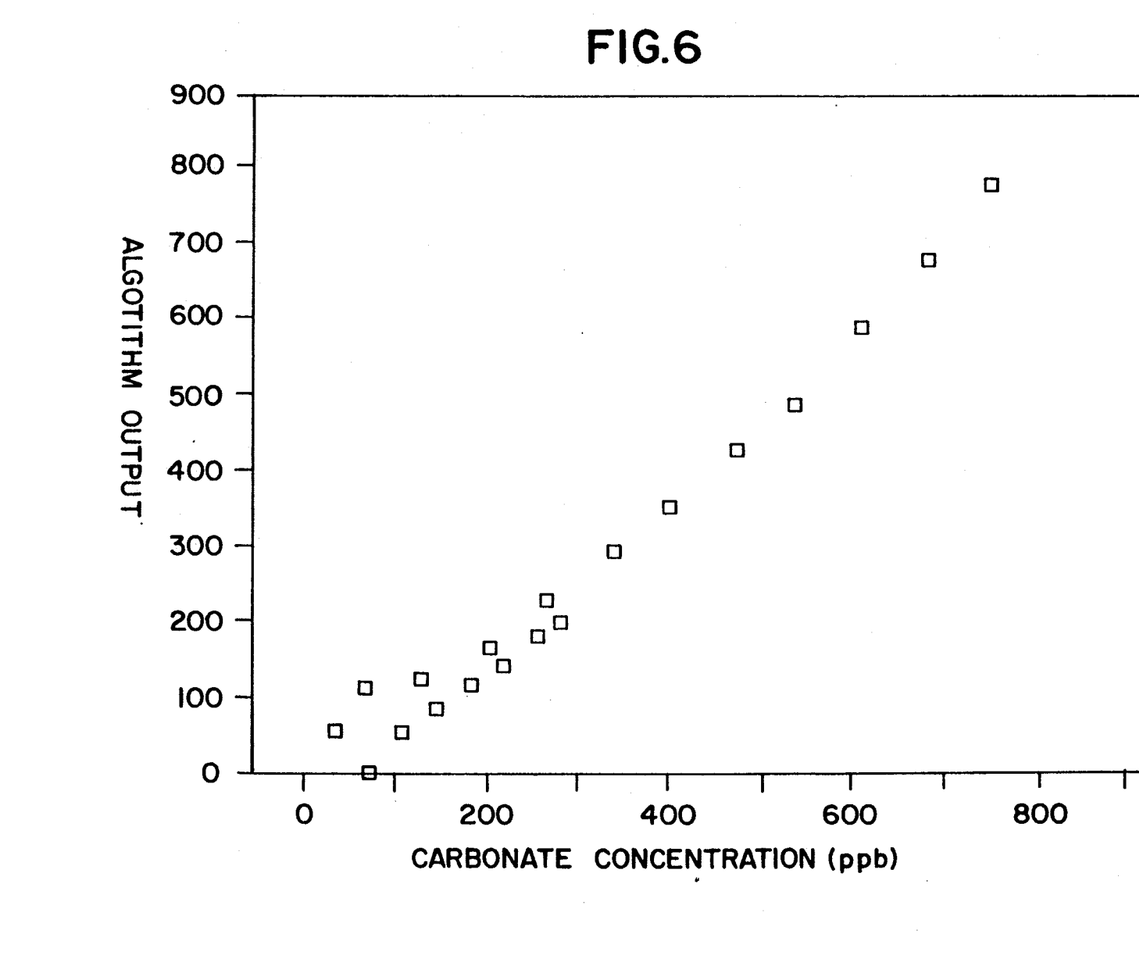
FIG. 6 is a graph showing test results of the present invention.

The reagent base used was 28 ppm ($1.97 \times 10^{-4}$M) sodium sulfate (weak base) 154. The membrane separator (110) was operated in accordance with the guidelines provided by the manufacturer. According to these guidelines, the dynamic concentration, i.e., molarity $\times$ flow, of the reagent should be at least five times that of the species in the test solution for which an exchange reaction is to be effected. The base strength used was chosen so that its dynamic concentrations would be at least five times that of the anticipated acid content of the test solution. For field operation, depending upon the expected content of the sample water, the base concentration may be adjusted. The results of several test runs using this method of carbon dioxide determination were plotted and are shown graphically in FIG. 6.

Referring back to FIG. 1, conductive species contributing to the total conductivity measured at cell (16) are $H^+$, $OH^-$, $SA^-$ (strong acid anions), and $HCO_3^-$ (bicarbonate). At cell (30), total conductivity is due to contributions from $H^+$, $OH^-$, $SA^-$, $HCO_3^-$ and $Na^+$.

The following observations and assumptions about this chemical system are made before deriving the $CO_2$ concentration from the two conductivity measurements.

A general basis of the method assumes that carbonic acid is the only weak acid in the sample and that the carbonate anion ($CO_3^-$) does not contribute significantly.

$Na^+$ at cell (30) is equal to $SA^-$; this assumes complete neutralization of strong acids.

The equivalent conductance of the strong acid anion is assumed to be that of chloride.

$SA^-$ concentration is the only constant concentration between cells (16) and (30); in all solutions of mixed (strong and weak) acid content, all other concentrations change in going from cell (16) to cell (30).

The target value is the total carbonate concentration. The concentration of the forms taken (carbonate, bicarbonate, undissociated carbonic acid) may change from cell (16) to cell (30) depending on the overall chemistry of the sample, but the target value, total carbonate, is a constant.

The unknown quantities in this chemical system are the following:

| | |
|---|---|
| $[H^+]_{16}$ | $[HCO_3^-]_{16}$ |
| $[H^+]_{30}$ | $[HCO_3^-]_{30}$ |
| $[SA^-]$ | $[OH^-]_{16}$ |
| $[Na^+]_{30}$ | $[OH^-]_{30}$ |
| C (the total carbonate concentration) | | where the subscripts (16) and (30) refer to the solutions passing through cells (16) and (30) respectively. This chemical system, then, requires nine independent relationships for a mathematical solution. These are listed below.

(1.) The water dissociation constant $$(\text{cell } 16) [H^+]_{16}[OH^-]_{16} = k_w$$

(2.)

$$(\text{cell } 30) [H^+]_{30}[OH^-]_{30} = k_w$$

(3.)

$$[Na^+]_{30} = [SA^-]$$

assuming total neutralization of the strong acid component of the sample (4.) Carbonate equilibrium at cell (16)

$$K = \frac{[H^+]_{16}[HCO_3^-]_{16}}{C - [HCO_3^-]_{16}}$$

(5.) Carbonate equilibrium at cell (30)

$$K = \frac{[H^+]_{30}[HCO_3^-]_{30}}{C - [HCO_3^-]_{30}}$$

(6.) Charge balance at cell (16)

$$[H^+]_{16} = [SA^-] + [HCO_3^-]_{16} + [OH^-]_{16}$$

(7.) Charge balance at cell (30)

$$[H^+]_{30} + [Na^+]_{30} = [SA^-] + [HCO_3^-]_{30} + [OH^-]_{30}$$

(8.) Let "M" equal the measured conductivity at cell (16)

$$M = \Lambda_{H^+}[H^+]_{16} + \Lambda_{OH}[OH]_{16} + \Lambda_{Cl}[SA^-] + \Lambda_{HCO_3^-}[HCO_3^-]$$

where $\Lambda$ is the equivalent conductance of the species indicated by the subscript (9.) Let "N" equal the measured conductivity at cell (30)

$$N = \Lambda_{H^+}[H^+]_{30} + \Lambda_{OH}[OH^-]_{30} + \Lambda_{Cl}[SA^-] + \Lambda_{HCO_3^-}[HCO_3^-]_{30} + \Lambda_{Na^+}[Na^+]_{30}$$

By measuring the conductivity of test solutions at cells (16) and (30), these nine simultaneous equations are solved and the total carbonate content of the solution determined. An algorithm solves this system of equations by an iterative method once values for M and N (cells (16) and (30) conductivities) are input. This algorithm runs on a Lotus ® spreadsheet.

Typically, the sample contains some amount of $CO_2$ (in water as carbonic acid) plus a variable amount of strong acids this assumes carbonic acid is the only weak acid.

The present technique is based on two conductivity measurements of the sample in two different conditions:
1. Carbonic acid plus strong acids
   Call this measurement "M".
2. Carbonic acid plus sodium salt of strong acids
   Call this measurement "N".

Conductivity at each point is equal to the sum of the concentrations of all conducting species times their respective conductance coefficients.

Valid only for low concentrations.
Conductive species contributing to "M":
   $H^+$, $OH^-$, $S^-$ (strong acid anions), $A^-$ (weak anions).
Conductive species contributing to "N":
   $H^+$, $OH^-$, $Na^-$, $S^-$, $A^-$.
(Note: $A^-$ = bicarbonate)

$$N = \Lambda_{H^+}[H^+]_N + \Lambda_{OH^-}[OH^-]_N + \Lambda_{S^-}[S^-] +$$
$$\Lambda_{A^-}[A^-]_N + \Lambda_{Na^+}[Na^+]$$

$$M = \Lambda_{H^+}[H^+]_M + \Lambda_{OH^-}[OH^-]_M + \Lambda_{S^-}[S^-] + \Lambda_{A^-}[A^-]_M$$

Unknowns $[H^+]_M$
$[H^+]_N$
$[OH^-]_M$
$[OH^-]_N$
$[A^-]_M$
$[A^-]_N$
$[S^-]$
$[Na^+]$
C (total carbonate concentration)
Note: let $\Lambda_{s^-} = 76.3$ (assume chloride)

Nine Unknowns

Known relationships:
(1)

$$[H^+][OH^-] = K_w = 1.02 \times 10^{-14}$$

(2)

$$[S^-] = [Na^+]$$

$$K_a = \frac{[H^+][A^-]}{C - [A^-]} \quad (3)$$

where:
C = total carbonate concentration—this is the target value
Two cases: solve quadratic for each Cell M, $[H^+] = [Na^+] + [A^-]$ 4. Then, $$[A^-]_M = \frac{-([Na] + K_a) + \sqrt{([Na] + K_a)^2 + 4K_aC}}{2}$$

Cell N, $[H^+] = [A^-]$

5. Then, $$[A]_N = \frac{-K_a + \sqrt{K_a^2 + 4K_aC}}{2}$$

Note: $[A^-]_N = [A^-]_M$ when $[Na^+] = 0$

6. $M = \Lambda_{H^+}[H^+]_M + \Lambda_{OH^-}\left(\dfrac{K_w}{[H^+]_M}\right) + \Lambda_S[Na^+] +$ $$\Lambda_A - \left\{\dfrac{-(K_a + [Na]) + \sqrt{(K_a + [Na])^2 + 4K_aC}}{2}\right\}$$

7. $N = \Lambda_{H^+}[H^+]_N + \Lambda_{OH^-}\left(\dfrac{K_w}{[H^+]_N}\right) + (\Lambda_S + \Lambda_{Na^+})[Na^+] +$ $$\Lambda_A - \left\{\dfrac{-K_a + \sqrt{K_a^2 + 4K_aC}}{2}\right\}$$

Charge balance at each cell:

8. Cell(16):

$[H^+]_M = [S^-] + [A^-]_M + [OH^-]_M$

9. Cell(30):

$[H^+]_N + [Na^+] = [A^-]_N + [S^-] + [OH^-]_N$

| SPREADSHEET AS DISPLAYED | | | |
|---|---|---|---|
| anions (chloride) | C(H) = | 350000 | |
| bicarbonate | C(X) = | 76000 | |
| | C(A) = | 44500 | |
| | C(Na) = | 50100 | −0.00171 |
| | [H]m = | 1.70E-05 | pH(cell 16) = 4.77 |
| | [H]n = | 8.53E-07 | pH(cell 30) = 6.07 |
| | [A](m) = | 6.43E-08 | |
| | [A](n) = | 8.53E-07 | |
| [X] = | [Na] = | 1.679E-05 | 608.2 |
| | K = | 4.60E-07 | |
| Cell 16 | M = | 7.221 | |
| Cell 30 | N = | 2.471 | |
| | C(M) = | 2.43E-06 | |
| | C(ppb) = | 146 | |

| SPREADSHEET CELL FORMULAS | |
|---|---|
| H13: | 'C(H) = |
| I13: | 350000 |
| F14: | 'anions (chloride) |
| H14: | 'C(X) = |
| I14: | 76000 |
| F15: | 'bicarbonate |
| H15: | 'C(A) = |
| I15: | 44500 |
| H16: | 'C(Na) = |
| I16: | 50100 |
| K16: | +I28−I13*I18-I14*I24−I15*I21−(I13*1.0200000E-14/I18) |
| H18: | '[H]m = |
| I18: | (S2) +I24+I21 |
| K18: | ' pH(cell 16) = |
| M18: | (F2) −@LOG(I18) |
| H20: | '[H]n = |
| I20: | (S2) (−I26_((I26) 2+4*I26*I32) 0.5)/2 |
| I20: | ' pH(cell 30) = |
| M20: | (F2) −@LOG(I20) |
| H21: | '[A](m) = |
| I21: | (S2) (−(I26+I24)+(I26+I24) 2+4*I26*I32) 0.5)/2 |
| H22: | '[A](n) = |
| I22: | (S2) (−I26+((I26) 2+4*I26*I32) 0.5)/2 |
| F24: | ' [X] = |
| H24: | '[Na] = |
| I24: | (S2) (I30−I13*I20−I15*I20−(I13*1.0200000E-14/I20))/(I14+I16) |
| J24: | (F1) +I24*36000000 |
| H26: | 'K = |

| SPREADSHEET CELL FORMULAS | |
|---|---|
| I26: | (S2) 0.00000046 |
| G28: | 'Cell 16 |
| H28: | 'M = |
| I28: | (F3) 7.221 |
| G30: | 'Cell 30 |
| H30: | 'N = |
| I30: | (F3) 2.471 |
| H32: | 'C(M) = |
| I32: | (S2) +I34/60000000 |
| H34: | 'C(ppb) |
| I34: | (FO) 146 |

| MACRO COMMANDS |
|---|
| {let d23,10}~ |
| {goto}E17~ |
| {LET D23,D23+100} |
| {EDIT} {CALC} |
| {if F5<0} {BRANCH IQ8163} |
| {LET D23,D23-10}~ |
| {EDIT} {CALC}~ |
| {IF F5>0} {BRANCH IQ8166}~ |
| {LET D23,D23+1}~ |
| {EDIT} {CALC}~ |
| {IF F5<0} {BRANCH IQ8169}~ |
| {LET D23,D23−.5}~ |
| {EDIT} {CALC}~ |
| {IF F5>0} {BRANCH IQ8172}~ |
| {beep} |
| {QUIT}~ |

The present invention provides several advantages over the currently employed degassed cation conductivity method. The first advantage is that the present invention is selective for weak acids since the method is based on thermodynamic considerations of acid-base relationships. Unfortunately, the present invention lacks the ability to distinguish between carbonic acid and other coexisting weak acids like acidic and/or formic acid. However, it is believed that by selection of appropriate reagent base strengths and dynamic concentration through the membrane/ion exchange separator, distinction among these acids may be feasible.

Figure 2:
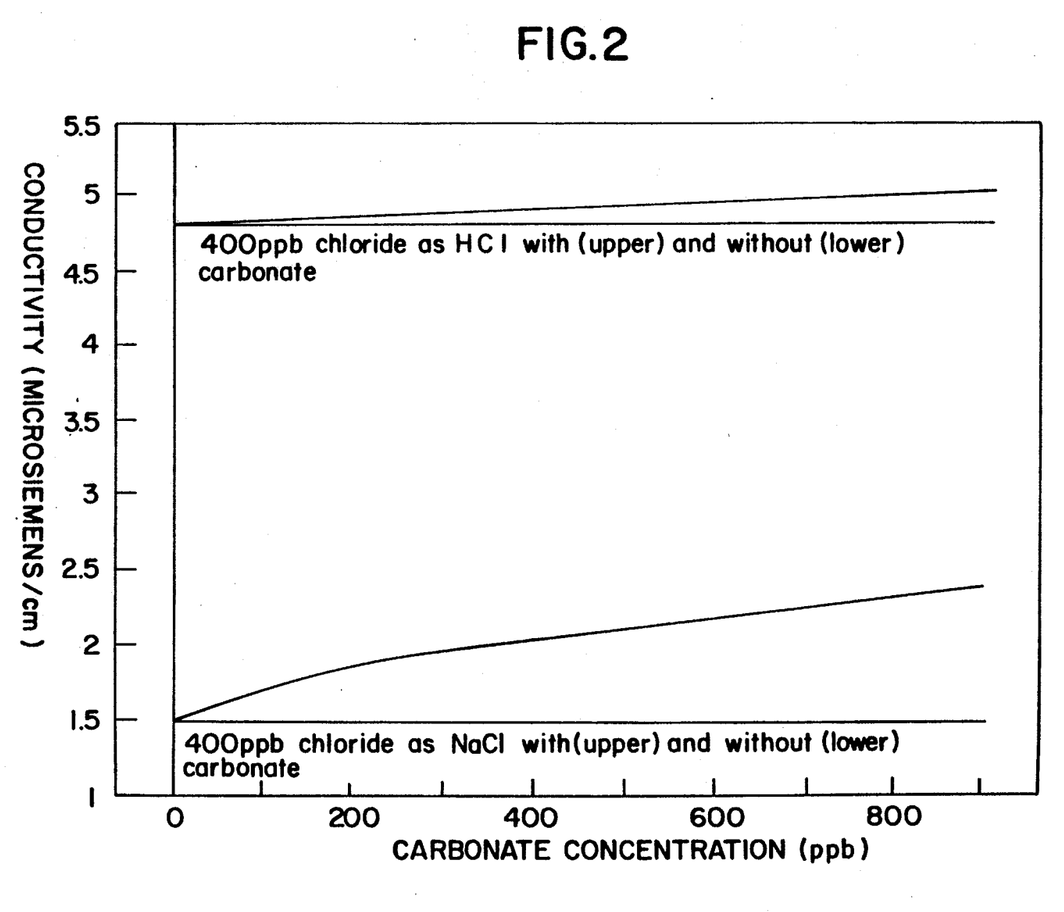
FIG. 2 is a graph showing the conductivity of carbonic acid in the presence of sodium chloride and the conductivity of carbonic acid in the presence of hydrochloric acid.

Another advantage of the present invention is higher precision in the interpretation of measured data obtained since the conductivity of carbon dioxide is greater after the membrane separator with a sodium salt background than it is before with the acid background. This advantage is demonstrated by referring to FIG. 2. FIG. 2 shows the conductivity of various levels of $CO_2$ in the presence of sodium chloride and in the presence of hydrochloric acid. The lower conductivity in the presence of hydrochloric acid is due to the suppressed dissociation of carbonic acid in this media. This is the parameter measured with the degassed cation conductivity method. By comparison, FIG. 2 illustrates the larger parameter measured with the present invention after any hydrochloric acid has been converted to sodium chloride.

Still another advantage of the present invention is that conductivity measurements are taken at ambient temperature which eliminates reliance on mathematical algorithms for the conversion of high temperature data. Additionally, there is no concern from potentially interfering high temperature reactions.

The foregoing example is intended for illustrative purposes and is not meant to limit the present invention only to this application.

While a specific embodiment of the invention has been shown and described in detail to illustrate the principles of the present invention, certain modifications and improvement will occur to those skilled in the art upon reading the foregoing description. It is thus understood that all such modifications and improvement have been deleted herein for the sake of conciseness and readability but are property in the scope of the following claims.

One example of such a modification would be to include a valve switching means connected to a solvent system for cleaning the apparatus after an analysis.

I claim:

1. A method for measuring low levels of carbon dioxide in a sample, comprising the steps of:
    passing a sample through a cation exchange resin;
    measuring the conductivity of the sample passed through the cation exchange resin for a first conductivity measurement indicative of a cation conductivity;
    supplying the sample passed through the cation exchange resin to a membrane separator, said membrane separator having a first compartment for receiving the sample and a second compartment separated by a membrane that allows for an exchange of ions between the compartments;
    supplying a weak base to said second compartment which ions cross the membrane to react with any strong acid in the sample and leave unreacted carbonic acid in the sample;
    taking a conductivity measurement of the sample exiting the first compartment of the membrane separator for a second conductivity measurement; and
    determining carbon dioxide concentration from a difference in the first and second conductivity measurements taken of the sample after it is passed through the cation exchange resin and after the sample exits the membrane separator.

2. A method as recited in claim 1, further comprising the step of measuring conductivity of the sample prior to passing it through the cation exchange resin to provide a specific conductivity measurement for an untreated sample in addition to the first and second conductivity measurements.

3. An apparatus for measuring low levels of carbon dioxide in a sample, comprising:
    means for exchanging cations for hydrogen connected to a sample stream;
    first means for measuring conductivity of the sample after it is passed through said cations exchanging means;
    a membrane separator connected to said first conductivity measuring means for receiving the sample, said membrane separator having a first and second compartment with said first and second compartments being separated by a membrane that allows for an exchange of ions between the compartments, said second compartment being constructed so as to supply a weak base to react with any strong acid in the sample and leave unreacted carbonic acid in the sample;
    second means for measuring conductivity connected to said membrane separator, said second conductivity measuring means taking a conductivity measurement of the sample after it exits the first compartment of said membrane separator; and
    means for determining carbon dioxide concentration in communication with said first and second conductivity measuring means for calculating carbon dioxide concentration from changes in conductivity of the sample after it is passed through the cation exchanging means and after it exits said membrane separator.

4. An apparatus as recited in claim 3, further comprising a third conductivity cell connected immediately before said exchanging means for measuring the specific conductivity of the untreated sample in addition to the first and second conductivity measurements.

* * * * *

UNITED STATES PATENT AND TRADEMARK OFFICE
CERTIFICATE OF CORRECTION

PATENT NO. : 5,252,491
DATED : Oct. 12, 1993
INVENTOR(S) : Dennis J. Connolly

It is certified that error appears in the above-identified patent and that said Letters Patent is hereby corrected as shown below:

In col. 1, line 50, delete "mal,n" and insert therefor --main--.

In col. 2, line 24, delete "L" and insert therefor --1--.

In col. 3, line 22, delete "(".

In col. 7, line 41, delete "$\Lambda^+$" and insert therefor --$+\Lambda$--.

In col. 7, line 50, delete "9".

In col. 8, line 11, delete "Na" and insert therefor --$Na^+$--.

Signed and Sealed this

Twenty-seventh Day of June, 1995

BRUCE LEHMAN

Attest:

Attesting Officer

Commissioner of Patents and Trademarks